United States Patent [19]
Wolf

[11] Patent Number: 5,225,322
[45] Date of Patent: Jul. 6, 1993

[54] IMMUNOASSAYS FOR DETECTION OF VIRAL SUBTYPES AND OTHER ANTIGENS

[75] Inventor: Benjamin Wolf, Broomall, Pa.

[73] Assignee: University of Pennsylvania, Philadelphia, Pa.

[21] Appl. No.: 833,626

[22] Filed: Feb. 7, 1992

Related U.S. Application Data

[63] Continuation of Ser. No. 271,935, Nov. 15, 1988, abandoned.

[51] Int. Cl.$^5$ .......................................... G01N 33/569
[52] U.S. Cl. .................................... 435/5; 435/7.22; 435/7.32; 435/7.5; 435/7.9; 435/7.92; 435/967; 435/975; 436/530; 436/547
[58] Field of Search .................. 435/5, 7.5, 7.92, 967, 435/975, 810; 436/514, 530, 531, 547; 530/412, 417, 826

[56] References Cited

U.S. PATENT DOCUMENTS

| | | | |
|---|---|---|---|
| 4,496,658 | 1/1985 | Kondo et al. | 436/510 |
| 4,727,037 | 2/1988 | Ring | 436/548 |
| 4,880,750 | 11/1989 | Francoeur | 436/501 |

OTHER PUBLICATIONS

Olsson, et al. "Improved Detection of Oligoclonal IgG In Cerebrospinal Fluid By Isoelectric Focusing In Agarose, Double-Antibody Peroxidase Labeling and Avidin-Biotin Amplification", Clin. Chem. 30/7, pp. 1246–1249 (1984).

A. R. Williamson, "Isoelectric Focusing Of Immunoglobulins", Handbook of Experimental Immunology, Chap. 9, pp. 9.1–9.31.

Briles, et al., "A Simple Method For Estimating The Probable Numbers of Different Antibodies By Examining The Repeat Frequencies Of Sequences Of Isoelectric Focusing Patterns", vol. 18 pp. 29–38.

Fucillo et al, "Rapid Viral Diagnosis" Manual of Clinical Laboratory Immunology 1986 pp. 489–496.

Nerurkar et al "Rapid Detection of Herpes Simplex Virus in Clinical Specimens by Use of a Capture Biotin-Streptavidin Enzyme-Linked Immunosorbent Assay," J. Clin Microbiol vol. 20(1) 1984 pp. 109–114.

Endo et al, "Fractionation of Polyclonal Antibody by Isoelectric Focusing–Differences in Cross–Reactivity and Affinity of Rabbit Clonotype Anti-human Thyrotropin Antibody" Analytical Biochemistry 143 1984 pp. 249–255.

Austin et al "Antigenic Mapping of an Avian H1 Influenza Virus Haemagglutinin and Interrelationships of H1 Viruses from Humans, Pigs and Birds" J. Gen. Virol 67 1986 pp. 983–992.

Hong, et al., "Dot-Immunobinding Assay With Monoclonal Anti-IgE Antibodies For The Detection And Quantitation Of Human Ige", Journal of Immunological Methods, 85:195–202 (1986).

Rordorf, et al., "A Multidot Immunobinding Assay For Autoimmunity And The Demonstration Of Novel Antibodies Against Retroviral Antigens In The Sera Of MRL Mice", Journal of Immunological Methods, 59: 105–112 (1983).

Towbin, et al., "Electrophoretic Transfer Of Proteins From Polyacrylamide Gel to Nitrocellulose Sheets: Procedure And Some Applications", Proc. Nat'l Acad. Sci. USA 76: 4350–4354 (1979).

(List continued on next page.)

*Primary Examiner*—David Saunders
*Assistant Examiner*—Carol E. Bidwell
*Attorney, Agent, or Firm*—Woodcock Washburn Kurtz Mackiewicz & Norris

[57] ABSTRACT

The invention provides methods for detection and identification of viruses, viral subtypes and other antigens. Polyclonal antibodies specific for a viral subtype are separated and then bound to a solid support. The antibodies are then contacted with a test sample suspected of containing the viral subtype. Virus particles binding to the separated antibodies are then detected and quantified. In other embodiments of the invention, a test sample suspected of containing an antigen is bound to a solid support, and then contacted with polyclonal antibodies specific for the antigen, the antibodies having a detectable label bound thereon. The detectable label is then detected. The invention also provides kits for performing the methods of the invention.

25 Claims, 6 Drawing Sheets

OTHER PUBLICATIONS

Towbin, et al., "Monoclonal Antibodies Against Eucrayotic Ribosomes, Journal of Biological Chemistry", 257:12709–12715 (1982).

Derer, et al., "Application Of The Dot Immunobinding Assay To Allergy Diagnosis", J. Allergy Clin. Immunol. 74: 85, (1984).

Van der Sluis, et al., "Press-Blotting On Gelatin–Coated Nitrocellulose membranes, A Method For Sensitive Quantitative Immuno-Detection of Peptides After Gel Isoelectric Focusing", Journal of Immunological Methods 104:65–71 (1987).

Blake, et al., "A Rapid, Sensitive Method For Detection Of Alkaline Phosphastase Conjugated Anti-Antibody On Western Blots", Analytical Biochemistry, 136: 175–179 (1984).

Stott, et al., "Isoelectric Focusing And Reverse Immunoblotting Of Autoantibodies Against High Molecular Weight Antigens".

Mehta, et al., "Identification Of Virus-Specific Oligoclonal Bands In Subacture Sclerosing Panencephalitis by Immuno-Fixation After Isoelectric Focusing And Perosidase Staining", Journal of Clinical Microbiology, 16: 985–987 (1982).

Jahn, et al., "A Quantitative Dot-Immunobinding Assay For Proteins Using Nitrocellulos Filters", Proc. Nat'l Acad. Sci. 81: 1684–1687 (1984).

Snyder, et al., "An Enzyme-Linked Immunosorbent Assay For The Detection Of Antibody Against Avian Influenza Virus", Avian Diseases 29:136–144 (1984).

Snyder, et al., "Rapid Serological Profiling By Enzyme-Linked Immunosorbent Assay III, Simultaneous Measurements Of Antibody Titers To Infectious Bronchitis, Infectious Bursal Diseases and Newcastle Disease Viruses In A Single Serum Dilution", Avian Diseases 28: 12–24 (1984).

Hazelgrove, et al., Anal. Biochem. 1509:449–456 (1985) "Rapid, Inexpensive, Quantitative, General-Purpose Densitometer and Its Application to One-Dimensional Gel Electrophoretograms".

Laver, "Purification Of Influenza Virus", in K. Habel and N. P. Salzman (eds) Fundamental Techniques in Virology, pp. 82–86 Academic Press, Inc. 1969.

Wolf, et al., "Non-allelic Inheritance of VH Region Group a Allotypes: Cell Surface And Serum Studies In Double and Triple Expressing Rabbits", J. Immunology 123:1858–1863 (1979).

Wolf, et al., "Clonal Diversity and Homology Of Latent And Nominal Group a Immunoglobulin Allotypes In The Rabbit", Mol. Immunol. 21:139–146 (1984).

Wabuke-Bunoti, et al., "Stimulation Of Anti-Influenza Cytolitic T Lymphocytes By CNBr Cleavage Fragments Of Viral Hemagglutinin", J. Immunol. 127:1122–1125 (1981).

IEF-TRANSBLOTTING ANALYSIS OF AVIAN INFLUENZA H5N2 EPITOPES

| | pI |
|---|---|
| | −7.1 |
| | −6.7 |
| | −6.4 |
| | −6.0 |
| | −5.7 |
| | −5.4 |
| | −5.1 |
| | −4.9 |

Rbt.  8406   8406   8401A1   8401A1   HEMO-GLOBIN CONTROL
      └── 16th BLEED ──┘  └── 16th BLEED ──┘
LANE   5      4       3        2         1

Figure 1:
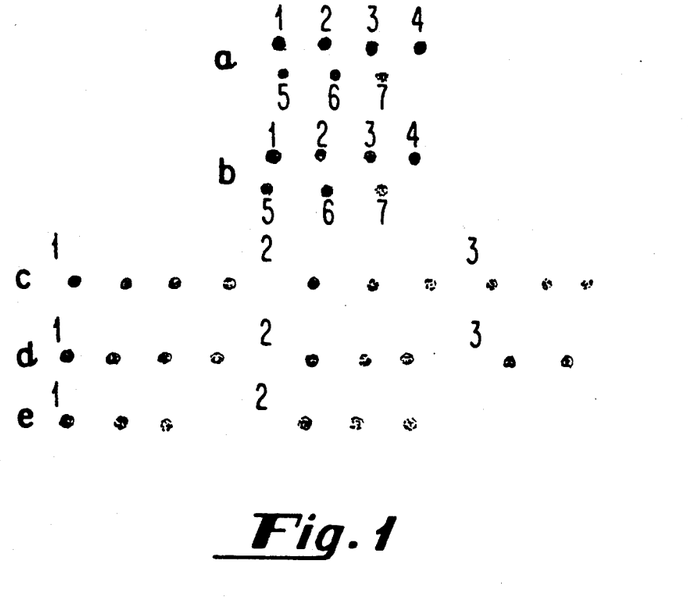
Figure 2A:
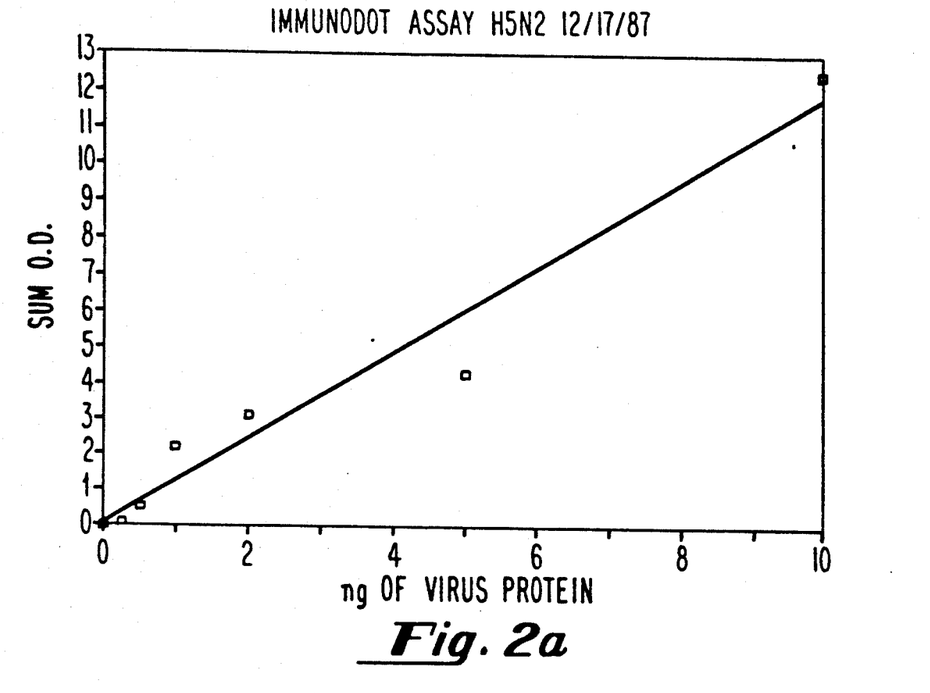
Figure 2B:
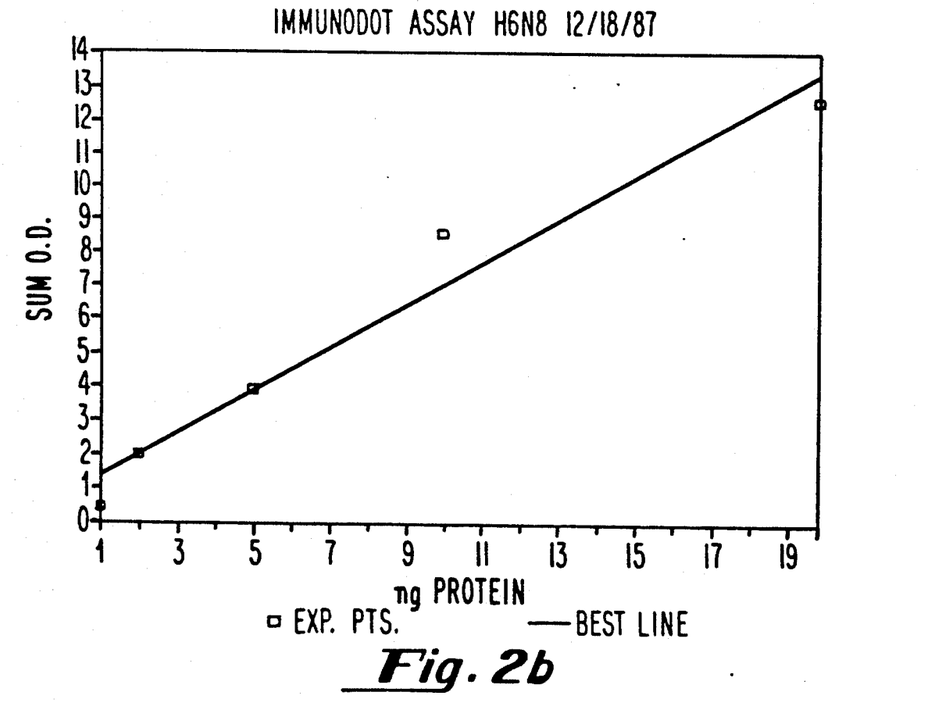
Figure 3A:
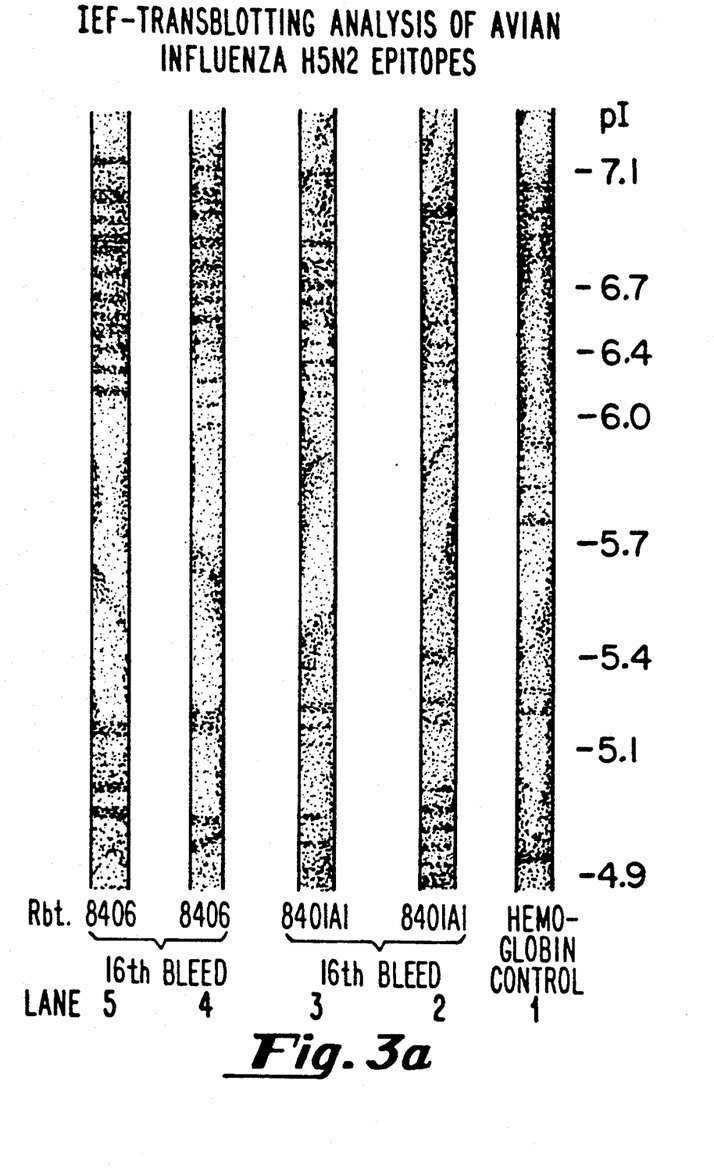

*Fig. 3a*

IEF-TRANSBLOT ANALYSIS OF AVIAN
INFLUENZA SUBTYPE EPITOPES

- 7.1
- 6.8
- 6.5
- 6.3
- 6.1
- 5.9
- 5.7
- 5.5

| H5N2 | H6N8 | H2N7 |
| MALLARD/NY/82 | Ty/Mn/83 | Ty/Mn/86 |
| LANE 3 | 2 | 1 |

Figure 4A:
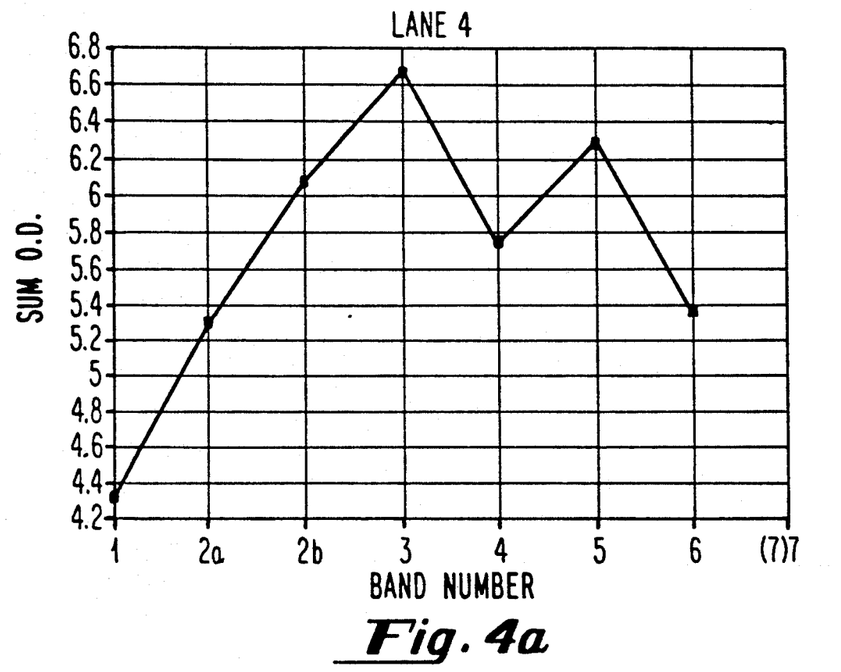
Figure 4B:
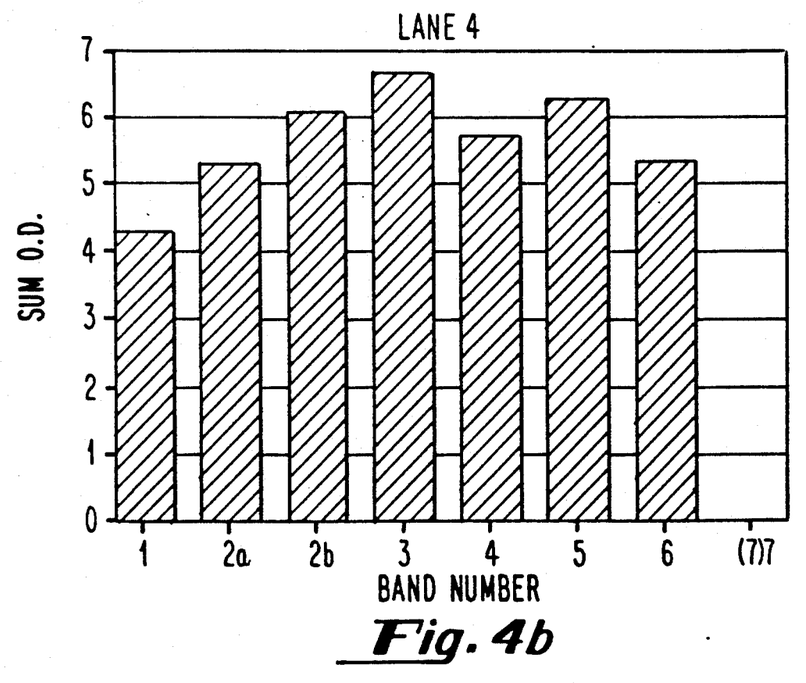
Figure 4C:
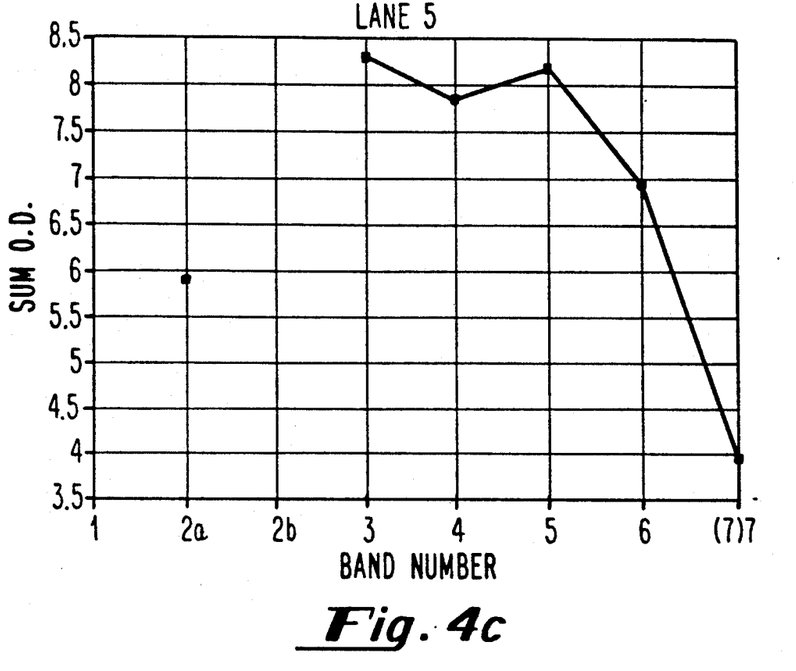
Figure 4D:
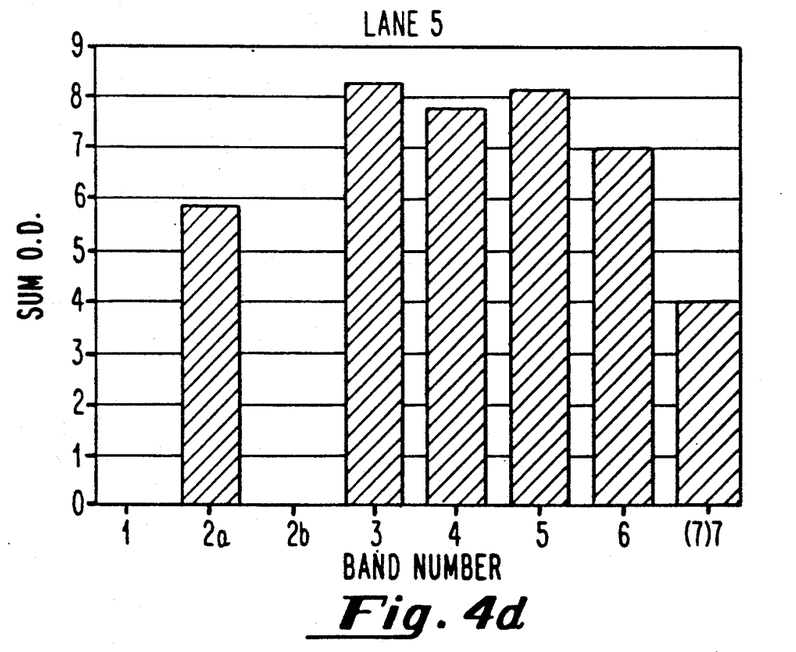

Fig. 4d

IMMUNOASSAYS FOR DETECTION OF VIRAL SUBTYPES AND OTHER ANTIGENS

GOVERNMENT GRANTS

The work presented in this patent application was supported in part by Department of Agriculture grant CRSR 2-2622. The United States government has certain rights in the invention.

This is a continuation of application Ser. No. 271,935, filed Nov. 15, 1988 now abandoned.

FIELD OF THE INVENTION

The present invention relates to the field of diagnostic methods for detection and identification of antigens and more particularly to the field of immunological methods for the detection and identification of antigens.

BACKGROUND OF THE INVENTION

It is often important and useful to be able to detect simultaneously the presence and concentration of one or more substances contained in a biological or chemical mixture. Immunoassays have proved to be important in detection of substances because of the specificity of antibodies used in the assays. Monoclonal antibodies, in particular, have increased the ability of immunoassays to detect a given substance since they can be selected to distinguish between even parts of a single molecule. Immunoassays can be designed to detect virtually any type of substance, providing it is antigenic or can be made antigenic by modification or conjugation with a larger antigenic, or carrier molecule. Examples of substances which can be detected are proteins, glycoproteins, peptides, oligosaccharides and living organisms, such as parasites, bacteria, protozoa and viruses. Further, substances such as drugs and other small molecules can be detected in immunoassays forming antibodies to a conjugate of the molecule and using the antibodies thus formed in the immunoassay.

In recent years a number of assays have been developed which employ antibodies to detect the presence of a wide variety of substances. Hong et al. "Dot-Immunobinding Assay with Monoclonal Anti-IgE Antibodies for the Detection and Quantitation of Human IgE", Journal of Immunological Methods, 95: 195-202, (1986), describes a dot immunobinding assay for determining human IgE with a tandem of monoclonal anti-IgE antibodies. Minute quantities of monoclonal anti-IgE antibodies were adsorbed on nitrocellulose discs. IgE bound to this solid phase monoclonal anti-IgE antibody was detected by a second monoclonal antibody conjugated with horseradish peroxidase. Using 4-chloro-1-naphthol as a chromogen resulted in a stable color reaction that was semiquantitative by the naked eye.

Rordorf et al., "A Multidot Immunobinding Assay for Autoimmunity and the Demonstration of Novel Antibodies against Retroviral Antigens in the Sera of MRL Mice", Journal of Immunological Methods, 59: 105-112, (1983), discloses immunobinding assay procedures for autoantibodies. In one assay viral proteins are electrophoresed and transferred to nitrocellulose. The nitrocellulose strips are then incubated with antisera and antibodies which bind to the viral proteins are detected by immunoperoxidase staining. The results of the assay can be quantitated with a densitometer. In another dot immunobinding assay, an antigen is applied to nitrocellulose. The nitrocellulose is incubated with sera and antibodies in the sera specific for the antigen are detected by immunoperoxidase staining.

Towbin et al., "Electrophoretic Transfer of Proteins from Polyacrylamide Gels to Nitrocellulose Sheets: Procedure and some applications", Proc. Natl. Acad. Sci. USA, 76: 4350-4354, (1979), discloses a method for the electrophoretic transfer of proteins from polyacrylamide gels to nitrocellulose. The transferred proteins are then detected by autoradiography.

Towbin et al., "Monoclonal Antibodies Against Eucaryotic Ribosomes", Journal of Biological Chemistry, 257: 12709-12715, (1982), discloses a dot immunoassay to isotype monoclonal antibodies. A series of antibodies to light and heavy chain immunoglobulin isotypes is dotted onto nitrocellulose. The nitrocellulose is then incubated with monoclonal antibody containing-hybridoma supernatants, where the anti-isotype specific antibodies will bind only to the monoclonal antibody exhibiting the specific isotype. The monoclonal antibodies bound are then detected by immunoperoxidase staining.

Derer et al., "Application of the Dot Immunobinding Assay to Allergy Diagnosis", J. Allergy Clin Immunol 74: 85, (1984), discloses dot immunobinding assays for detection of IgE and allergen-specific IgE. Antibodies to IgE are dotted onto a solid phase and then incubated with patient's serum. Antibodies from the serum which bind are detected by immunoperoxidase staining.

Van der Sluis et al., "Press-Blotting on Gelatin-Coated Nitrocellulose Membranes, a Method for Sensitive Quantitative Immunodetection of Peptides after Gel Isoelectric Focusing", Journal of Immunological Methods 104: 65-71, (1987), presents a method for the fixation of peptides in nitrocellulose membranes after isoelectric focusing on thin polyacrylamide gels. Focusing gels are covered with a gelatin-coated nitrocellulose membrane. Using glutaraldehyde, focused peptides are covalently fixed onto this membrane. Fixed peptides are stained using the peroxidase-anti-peroxidase method and the immunoreaction is quantitated by rendering the membrane transparent and measuring the optical density of the precipitated chromogen in each band.

Blake et al., "A Rapid, Sensitive Method for Detection of Alkaline Phosphatase-Conjugated Anti-antibody on Western Blots", Analytical Biochemistry, 136: 175-179, (1984), discloses a method for the detection of antibody-antigen complexes on Western blots using alkaline phosphatase and chromogenic substrate.

Stott and McLearie, "Isoelectric Focusing and Reverse Immunoblotting of Autoantibodies Against High Molecular Weight Antigens", Immunological Investigations 15: 113-122, (1986), discloses a method for the clonal analysis of antibodies against high molecular weight antigens This method involves isoelectric focusing, electrophoretic transfer of the focused antibodies to a nitrocellulose membrane and detection of the membrane-bound antibodies by overlay with radiolabeled antigen (reverse immunoblotting). The application of this technique to the clonal analysis of autoantibodies against thyroglobulin and DNA is described.

Mehta et al. "Identification of Virus-specific Oligoclonal Bands in Subacute Sclerosing Panencephalitis by Immunofixation after Isoelectric Focusing and Peroxidase Staining", Journal of Clinical Microbiology, 16: 985-987, (1982), discloses a method for detecting antibodies with specific activity against viral and other antigens in oligoclonal bands in cerebrospinal fluid and serum. Serum and cerebrospinal fluid were subjected to isoelectric focusing and immunofixation with measles virus. The gel was stained with horseradish peroxidase-conjugated goat antihuman immunoglobulin G.

U.S. Pat. No. 4,727,037 issued Feb. 23, 1988 to Ring discloses a method for determination of the isotype (class) for a panel of monoclonal antibodies. The assay comprises adsorbing on a solid support medium antibodies directed to specific immunoglobulin heavy and light chains. The solid support medium is then incubated with the monoclonal antibody of interest which will bind to the specific antibody for its isotype Monoclonal antibody bound to the solid support medium is then visualized with a chromogenic substrate.

Jahn et al., "A Quantitative Dot-Immunobinding Assay for Proteins using Nitrocellulose Filters", Proc. Natl Acad. Sci. 81: 1684–1687, (1984), discloses a method for detection of synapsin I. In this method samples of synapsin I (from rat brain synaptic vesicles) were dot blotted onto a solid phase, then an overlay antibody was bound to the synapsin I, followed by $I^{125}$-labelled protein A. The dot blots were then quantitated by assaying for radioactivity. About 50 ng antigen (synapsin I) was detectable. The specificity of the system was not probed.

Snyder et al., "An Enzyme-Linked Immunosorbent Assay for the Detection of Antibody Against Avian Influenza Virus", Avian Diseases 29: 136–144, (1984), and Snyder et al., "Rapid Serological Profiling by Enzyme-linked Immunosorbent Assay. III. Simultaneous Measurements of Antibody Titers to Infectious Bronchitis, Infectious Bursal Diseases and Newcastle Disease Viruses in a Single Serum Dilution", Avian Diseases 28: 12–24, (1984), disclose an immunoassay for detecting avian viral infection. Virus is bound to a solid support, and serum containing antibodies to the virus is contacted with the bound virus. Antibodies are detected by binding enzyme-linked immunoglobulin to the antibodies and supplying the enzyme with substrate.

Although monoclonal antibodies have proven useful in immunoassays because of their specificity, the use of monoclonal antibodies for detecting and distinguishing between large antigens having multiple antigenic determinants or epitopes has several drawbacks. If the test antigen, such as a virus has mutated and does not contain or if the antigenic determinant corresponding to the monoclonal antibody in the assay has been modified, an accurate result would not be obtained. Similarly, if the monoclonal antibody used in the assay has a specificity corresponding to a shared antigenic determinant, the assay may not be able to distinguish between closely related antigens having multiple antigenic determinants. Distinguishing between the two would require time consuming procedures to find monoclonal antibodies not common to the large antigens. Immunoassays that overcome these drawbacks, but which preserve the advantages of antibody specificity are clearly needed. This need is especially apparent in assays for detection of living organisms, such as viruses, which change over time.

Viral infection and resultant disease cause much suffering to the affected individuals, whether human or animal. Much effort has been directed to development of methods for detecting and identifying viruses in humans and animals so that treatment and containment of the virus can begin as soon as possible to alleviate suffering and reduce spread of the viral disease.

Viral disease can create the potential for huge economic losses when the infected individuals are an important agricultural species such as the chicken. The poultry industry of the United States is a 10 billion dollar year business which continues to be threatened by outbreaks of highly pathogenic (Fowl Plague) influenza virus infections. Avian influenza (AI) virus disease creates enormous epidemiologic, pathogenic and economic impact throughout the poultry industry.

Avian influenza virus has created problems for the poultry industry for many years. Outbreaks of the virus have been sporadic. The disease, not seen in the United States since 1929, reappeared in Pennsylvania in 1983. The disease has spread from Pennsylvania to Maryland, Virginia, and New Jersey and threatens to spread to the entire United States.

The avian influenza virus occurs in several subtypes and strains, only some of which cause virulent disease. During a disease outbreak, serious problems of determining the pathogenicity of a particular viral type isolated from an infected bird are encountered. The virus isolated from a bird must be "pathotyped" by the time-consuming method of observing inoculated birds or embryos. In the 1983 Pennsylvania outbreak of influenza, delay in recognizing the potential virulence of the H5N2 isolate, the pathogenic subtype, was responsible for the extensive spread of the disease prior to the implementation of the quarantine and eradication program. The isolation of additional subtypes and mutants of influenza viruses from healthy and sick birds has brought near panic for regulatory officials. Officials must decide whether the isolate is a subtype or mutant strain of the avian influenza virus that represents a serious threat requiring dramatic action such as an eradication program or whether a wait-and-watch attitude should be taken. More rapid methods of detecting avian influenza virus, and other viruses are urgently needed to overcome the problems associated with delay in diagnosing the viral subtype.

A variety of assays, including pathotyping as well as serological testing for virus surface proteins, i.e. the hemagglutinins and neuraminidases, are presently employed in order to distinguish between virus subtypes. The assays require highly experienced personnel and sophisticated equipment. In addition, existing serological assays such as agar gel precipitation and hemagglutination inhibition are often insensitive and may not accurately distinguish among isolates.

Tests using monoclonal antibodies have also been developed for antigenic analysis of viruses. Monoclonal antibodies are powerful because of their unequivocal specificity. Clear-cut antigenic differences between closely related viruses can be made in otherwise indistinguishable strains. For instance, antigenic differences between vaccine and field strains of rabies virus have been demonstrated by monoclonal antibodies when whole serum antibodies failed. Relationships of distantly related viruses can also be determined with monoclonal antibodies. Antigenic maps which show the relationship of antigenic determinants on one protein can also be constructed and related to genetic differences. However, the use of monoclonal antibodies for detecting different viral subtypes has several drawbacks. It has been found that some monoclonal antibodies for H5N2, a strain of avian influenza virus did not react with other H5N2 viruses. This is presumably because the reactive epitope(s) has been deleted in the other viruses. Another drawback of monoclonal antibody analysis of viruses in addition to the findings on H5N2 mentioned above, is the large number of different monoclonals needed to test the virus adequately. Monoclonal antibodies are very time-consuming to produce and the specificity and cross-reactivities cannot be controlled except by lengthy selection procedures. Also, mutations can not be picked up unless the panel of monoclonal antibodies being used happens to have a specificity for the critical antigenic determinant.

Despite the efforts which have been made to develop accurate tests for detecting viruses, tests are required which can be performed accurately and with minimal need for specialized equipment. Tests which can be performed in the field are also needed. Poultry growers are often located far from research centers and agriculture department stations. Tests which can be performed in the field would allow poultry growers to avoid delay in treating birds and taking precautions for preventing the spread of the virus. Whether in the field or the laboratory, there is also a great need for tests which can accurately and rapidly distinguish between pathological and non-pathological subtypes of avian influenza virus.

The problems in providing fast accurate tests to detect avian influenza virus are also encountered in immunoassays for other substances, particularly if the substance contains multiple antigenic determinants or epitopes, such as would be present in living organisms and larger molecules. Although monoclonal antibodies are valuable for distinguishing between closely related organisms, immunoassays using monoclonal antibodies may give inaccurate results if the test sample contains an organism not having the epitope corresponding to the monoclonal antibody employed in the assay. This situation could easily arise if there has been a mutation in the organism deleting or modifying the antigenic determinant.

It is an object of this invention to provide novel methods for detection, identification and quantitation of antigens and hence the source or organism containing the antigen, such as viral subtypes and strains. It is also an object of the invention to provide novel methods for detecting, identifying and quantitating avian influenza virus subtypes and strains. It is a further object of the invention to provide kits for use in detecting, identifying and quantitating antigens and hence the organism containing the antigen, such as viruses, viral subtypes and strains.

BRIEF DESCRIPTION OF THE DRAWINGS

FIGS. 1*a* and 1*c* show the dot blot assay for avian influenza virus strain H5N2/Mal/NY/82, FIGS. 1*b* and 1*d* show the dot blot assay for avian influenza strain H6N8/Ty/Mn/83 and FIG. 1*e* shows the dot blot system for H2N7/Ty/Mn/86.

FIGS. 2*a* and 2*b* show quantitative representation of two viral proteins after computer-analyzed digitization.

FIG. 3A show a transblot of hyperimmune sera of two rabbits injected with avian influenza H5N2/Mal/-NY/82 where the virus is adsorbed onto nitrocellulose and probed with biotinylated antibodies and FIG. 3B shows transblot of three different subtypes of avian influenza virus analyzed with a single virus to determine epitope differences among the subtypes.

FIGS. 4*a* and 4*b* show line and bar graphs, respectively, of the bands of lane 4 in FIG. 3*a* that have been quantitated by densitometry and computer-digitized. FIGS. 4*c* and 4*d* show line and bar graphs, respectively, of the bands of lane 5 in FIG. 3*a* that have been quantitated by densitometry and computer-digitized.

SUMMARY OF THE INVENTION

The invention provides methods of detecting an antigen in a test sample suspected of containing said antigen, and hence the source or organism containing the antigen. Polyclonal antibodies specific for the antigen are separated and then applied to a solid support. The separated antibodies are then contacted with a test sample suspected of containing the antigen under conditions selected to allow binding of the antigen to the antibodies. Antigen bound to the antibodies on the solid support is then contacted with antibodies specific for the antigen under conditions selected to allow binding of the antibodies to the bound antigen. The antibodies to the antigen used in this step have a detectable label bound thereon. The detectable label is then detected. A preferred antigen is viral protein; a preferred virus is avian influenza virus.

The methods may further comprise the step of removing antibodies cross-reactive with antigens other than the antigen being tested from the polyclonal antibodies before the first separating step. The methods may also comprise the step of quantitating the amount of detectable label thereby quantitating the amount of the antigen present in the test sample and thus the amount of the organism containing the antigen in the test sample. A preferred method of quantitation is by densitometric measurement. Methods of separating antibodies known in the art are suitable for use in the invention. A preferred method is isoelectric focusing because this method accurately separates antibodies in polyclonal antisera into bands containing only one type of antibody, i.e. each band acts like a separate "monoclonal" antibody.

The methods of the invention are suitable for use with detectable labels and detection systems and methods known in the art. A preferred detectable label is biotin and a preferred method for detecting the detectable label comprises the steps contacting the biotin with streptavidin-alkaline phosphatase under conditions selected to allow the streptavidin-alkaline phosphatase to bind to the biotin; contacting the streptavidin-alkaline phosphatase with a chromogenic substrate; and detecting a reaction product of the chromogenic substrate.

Part of the mammalian immunologic response to an antigen is to produce antibodies specific for the antigen. An antigen is material that elicits antibody production. Proteins, polysaccharides and nucleic acids are usually effective antigens. The specificity of an antibody is directed against a particular site on an antigen called the antigenic determinant. An antigen may contain multiple antigenic determinants. In proteins, an antigenic determinant may comprise only six or seven amino acids of the protein. As used herein, the term antigen includes proteins, polysaccharides, nucleic acids and other cellular components capable of provoking an immune response, as well as microorganisms, such as viruses, which are also capable of provoking an immune response. The term antigen also includes substances not capable of provoking an antigenic response, i.e. haptens, but which are capable of provoking an antigenic response when conjugated with a carrier molecule.

A typical virus, for example, has multiple antigenic determinants within the proteins which make up its outer envelope (as well as internally) that provoke a multitude of different antibodies in the host mammal. In addition, different antibodies are produced to each antigenic determinant in a single macromolecular antigen, depending upon which part of the antigen provoked the antibody response. The sum of this response to the virus theoretically represents antibodies made to all the antigenic determinants present on the virus, including those shared by other viruses and those belonging only to that particular viral type or subtype. When these polyclonal antibodies are separated by techniques such as isoelectric focusing or other techniques to form bands of antibodies each having its own identifiable electric charge, and visualized; the antibodies form a "fingerprint" of the virus which can be used to distinguish it from other viruses or viral subtypes and strains. The use of a spectrum of antibodies to the virus overcomes problems associated with monoclonal antibodies such as the need for a number of monoclonal antibodies to adequately type the virus, loss of specificity through mutation of the virus, or lack of specificity for different isolates of the same viral subtype. By using a wide variety of antibodies to one virus, a change in one or a small number of antibodies is less noticeable overall. This ensures that the results of detection methods using the viral "fingerprint" will remain reliable and accurate even if some changes in the virus occur. Additionally, by removing antibodies to shared antigenic determinants from the polyclonal antibodies before separation, only antibodies to those antigenic determinants not shared by the two strains will remain in the serum. This step is especially useful for identification of closely related strains as it removes shared antibodies and makes the differences between the strains more apparent.

The methods of the invention can be used with any type of antigen that provokes the production of more than one type of antibody. The polyclonal response to the antigen, when the antibodies are separated, represents the antigen's "fingerprint" and can be used to identify the antigen. The number of antibodies in the antigen's "fingerprint" is related to the number of antigenic determinants in the antigen. A protein, for example, would produce a "fingerprint" having fewer types of antibodies than a larger antigen such as a virus which has a number of proteins containing multiple antigenic determinants in its outer envelope. Examples of protein antigens are enzymes, such as neuraminidase; blood coagulating proteins such as hemagglutinin; and viral envelope proteins, such as described for avian influenza virus herein.

The invention also provides further methods of detecting an antigen in a test sample suspected of containing the antigen. A test sample suspected of containing the antigen is bound to a solid support. The test sample is then contacted with polyclonal antibodies specific for the antigen, the antibodies having a detectable label bound thereon, under conditions selected to allow binding of the antibodies to the antigen in the tissue sample. The detectable label is then detected, thereby identifying the antigen.

The methods may further comprise the step of quantitating the amount of the antigen present in the test sample. The methods may also further comprise the step of removing antibodies cross-reactive with antigens other than said antigen from the polyclonal antibodies before contacting the test sample with the antibodies. These methods are suitable for use with detectable labels and detection systems and methods known in the art. A preferred detectable label is biotin and a preferred method of detection of the detectable label comprises the steps contacting the biotin with streptavidin-alkaline phosphatase under conditions selected to allow the streptavidin-alkaline phosphatase to bind to the biotin; contacting the streptavidin-alkaline phosphatase with a chromogenic substrate; and detecting a reaction product of the chromogenic substrate. A preferred method of quantitating the detectable label is by densitometric measurement. A preferred solid support is nitrocellulose.

The methods of the invention are suitable for use with antigens which provoke the production of more than one type of antibody. Examples of suitable antigens are proteins such as viral envelope proteins, infectious organisms and other molecules which provoke an immunogenic response. A preferred antigen is viral protein; a preferred virus is avian influenza virus. If the substance to be detected is not itself antigenic, it can be made antigenic by conjugation to a carrier molecule, such as bovine serum albumin, using conventional techniques.

The invention further provides kits for the detection of an antigen in test samples suspected of containing the antigen. The kits comprise separated polyclonal antibodies of the antigen bound to a solid support; a reagent comprising antibodies specific for the antigen having a detectable label bound thereon: at least one reagent comprising means for detecting for the detectable label; and a reference standard of the antigen comprising polyclonal antibodies of the antigen bound to a solid support, the antigen bound to the polyclonal antibodies and the antigen detected by the reagents of the kit. The form of the kit will depend on the assay to be performed. For the "fingerprinting" assay, the polyclonal antibodies would be separated and bound to a solid support. The solid support would be nitrocellulose or other suitable solid support. Each kit would contain one or more antigen "fingerprints". For each antigen to be tested, the reagent would contain antibodies for the antigen, the antibodies having a detectable label bound thereon. The antibodies for each antigen may be supplied together in one container or in separate container. The detectable label may be any of those known in the art for detection of antibodies which does not substantially interfere with the function of the antibody to detect the virus. The reagent for comprising means for detecting the detectable label would be coordinated with the detectable label to form a detection system for the antibodies. Some suitable detection systems may require more than one reagent for detection of the detectable label, in which case the additional reagents would also be supplied in the kits. Examples of suitable detectable labels and detection systems are those described herein. A kit for the detection of a virus, such as a strain of avian influenza virus, would comprise separated polyclonal antibodies specific for that strain bound to a solid support; a reagent comprising antibodies specific for the strain of avian influenza virus having a detectable label such as streptavidin-alkaline phosphatase conjugate bound thereon; a reagent comprising nitroblue tetrazolium (NBT); a reagent comprising 5-bromo-4-chloro-3-indolyl phosphate (BCIP); and a reference standard comprising polyclonal antibodies of the viral strain bound to a solid support, the virus bound to said polyclonal antibodies and said viral strain detected by the reagents of the kit. The reagents of the kit are designed to be used in sequence to achieve the desired color.

The invention also provides other kits for detecting an antigen in a test sample suspected of containing the antigen. The kits comprise a solid support onto which the sample suspected of containing an antigen is applied, a reagent comprising antibodies specific for said antigen having a detectable label bound thereon; at least one reagent comprising means for detecting the detectable label; and a reference standard of the antigen comprising the antigen bound to a solid support and detected by the reagents in the kit.

Suitable solid supports are nitrocellulose and other solid supports known in the art. The reagent containing antibodies specific for the antigen may contain antibodies for one or more antigens, depending on whether the kit is being provided to detect antigens. If the kit is designed to detect more than one antigen, the reagent containing antibodies having a detectable label bound thereon may be supplied in separate containers for each antigen. The reagent comprising the substrate for the detectable label would be coordinated with the detectable label to form a detection system. Some suitable detection systems may require more than one reagent for detection of the detectable label, in which case the additional reagents would also be supplied in the kits. Examples of detectable labels and detection systems suitable for use in the reagents of the kit are those described herein. Suitable solid supports are nitrocellulose and other solid supports known in the art. The methods of the invention, which are to be performed by the reagents included in the kit, are performed on the solid support.

For both the "fingerprinting" assay and the dot blotting assay, if the kit is to be used in the field away from the laboratory, a chromogenic detection system, such as a system employing alkaline phosphatase is preferred. For example, separate vials containing streptavidin-alkaline phosphatase conjugate in buffer, nitroblue tetrazolium (NBT), and 5-bromo-4-chloro-3-indolyl phosphate (BCIP), which are designed to be used in sequence to achieve the desired color could be supplied as part of the kit. With chromogenic detection systems such as these, the antibodies can be visualized by eye without the aid of any equipment. With chromogenic detection systems, the kit can be used in the field, and the solid support, containing the test performed using the kit of the invention later transported to a laboratory for quantitation of the amount of virus present in the test sample.

If it is desired to quantitate the amount of antibody present and thus the amount of virus present when performing the methods of the invention, a detection system employing alkaline phosphatase is preferred. As shown herein, a system employing alkaline phosphatase will give accurate quantitative results when used in conjunction with a densitometer.

In general, however, the detectable label may be any ligand or hapten which is capable of being detected, directly or indirectly and thereby indicate that binding of the antibody to the virus has occurred. Haptens are compounds having a molecular weight of approximately 6,000 or less and which are not large enough to provoke an immunogenic response, but which need to be conjugated to a carrier substance in order to provoke the immunogenic response. Haptens are thus antigenic determinants and may be adsorbed by isolated antibodies specific to them, even though the haptens are not conjugated to the carrier. A preferred label is biotin and it may be detected as described herein. Other methods of detecting biotin known in the art are also suitable for use in the methods of the invention. The detectable label may also be an enzyme capable of causing a color change in a substrate solution. Suitable enzymes are horse radish peroxidase and alkaline phosphatase. The detectable label may also be a radioactive molecule such as $^{32}P$, $^{125}I$ or $^{3}H$, a fluorescent molecule, such as fluorescein, a chemilluminescent molecule, such as luciferin or a light scattering molecule, such as colloidal gold. Suitable detection methods and systems are scintillation counting, autoradiography, fluorescence measurement, colorimetric measurement or light emission.

Polyclonal antibodies suitable for use in the methods of the invention may be produced and purified by conventional antibody production methods. Rabbits and mice are suitable animals for production of antibodies. Larger animals such as goats and sheep are also suitable if larger quantities of antibodies are needed.

Examples of test samples suspected of containing an antigen which are suitable for use in the methods and kits of the invention are body fluids, body tissues such as lung, spleen and kidneys, and other samples suspected of containing antigens which are soluble or may be suspended in a suitable fluid, such as a buffer, for use in the methods and kits.

Avian influenza virus may be obtained from chickens infected with the virus. Alternatively, the virus may be obtained from government laboratories such as the National Veterinary Services Lab, Ames, Iowa.

The solid support used in the methods of the invention may be made of any material to which antibodies and the antigen are capable of binding, but which does not substantially interfere with the detection of the antigen. Examples of suitable supports are nitrocellulose, unmodified nylon, cationized nylon carrying a quaternary amino charge (Zeta probe), and aminophenylthioether (APT) paper which is converted to DPT, the diazo derivative (this cannot be stained for use with enzyme detectable labels). The solid support generally will be in the shape of a strip or sheet, but other shapes are suitable.

The methods of the invention are conveniently performed with conventional commercially-available apparatus. For quantitating the amount of detectable label present, and thus the amount of antigen present, the procedure and apparatus of Hazelgrove et al., Anal. Biochem 150:449-456, 1985) are preferred. This procedure is based on a TV camera linked to a computer. The dots are displayed on a light box imaged by the TV camera, and digitized with a digitizing board (Techmar, Inc.). After digitizing, the computer will readout the position, width, height and relative area of each dot. Optical density (OD) measurements are plotted against absolute protein concentrations.

EXAMPLES

Growth and purification of influenza virus subtypes

An apathogenic strain, H5N2, (A/Mal/189/82), was provided by Dr. Robert G. Webster. Other avian apathogenic subtypes, H6N8, (A/Ty/Mn/6020-1604/81, H2N7 (A/Ty/Mn/1136/86), H1N1 (A/Ty/Ks/4880/80); the index case virus for the Pennsylvania outbreak of 1983, H5N2 (A/CK/PA/83); H5N2 (A/Ty/Mn/87); H7N3 (A/Ty/Or/71), as well as a number of H5N2 isolates were sent by Dr. Jim Pearson, National Veterinary Services Lab (NYSL), Ames, Iowa.

The viruses were grown in chicken embryos, purified by elution from chicken erythrocytes, followed by sedimentation through a sucrose gradient, 10% through 40%, 0.15M NaCl, following the procedure of Laver, W.G., "Purification of influenza virus", in K. Habel and N.P. Salzman (eds.) Fundamental Techniques in Virology, pp.82-86, Academic Press, Inc., 1969. Lack of associated chick proteins was seen in the virus preparations as determined by ELISA, since anti-chicken ovalbumin antibodies, sensitive at 1-5 nanograms, did not detect any ovalbumin from chick embryos, in the purified virus preparations, using the dot blot assay for chicken albumin.

PREPARATION OF ANTIBODIES

Immunization of rabbits

Rabbits were injected intradermally with virus (hemagglutinin titers 1:512-1:1024) initially in Freund's complete adjuvant, followed by virus in incomplete Freund's adjuvant at biweekly intervals.

Purification of anti-viral antiserum

Purified viruses are covalently linked to the solid matrix, Affi-Gel 10 (Bio-Rad Laboratories, Richmond, CA), which consists of agarose beads containing the spacer N-hydroxy-succinimide. Rabbit anti-viral antisera are absorbed to columns containing the virus-bead conjugate, the beads are washed extensively, and the purified antibodies are eluted in glycine-HCl, pH 2.3, following the procedure of Wolf et al., "Non-allelic inheritance of VH region group a allotypes: cell surface and serum studies in double and triple expressing rabbits", J. Immunology 123: 1858–1863,(1979).

Cross absorption of anti-viral antiserum

Antiviral antisera are also purified by cross-absorption for which either non-biotinylated or biotinylated IgG are mixed with 100 ul of a suspension of a virus (40 nanograms/100 ul), this virus being of a type different than the virus which was used to make the antiserum. The mixture is incubated at 37° C. for 2 hours and overnight at 4° C., after which the non-absorbed antibodies are separated after centrifugation of virus-antibody complex at 100,000 ×g. This procedure has been useful in deriving antibodies for private epitopes or antigenic determinants found on a particular viral subtype, after elimination of antibodies to public epitopes or those antigenic determinants shared by both viruses.

Biotinylation of affinity-purified antiviral antibodies or Immunoglobulin (IgG)

The antibodies or IgG (1 mg in 1 ml in 0.lM $NaHCO_3$) are reacted with biotin-N-hydroxy succinimide ester, dissolved (200 ug/200ul) in dimethyl sulfoxide. The mixture remains at room temperature for 4 hours and this is dialyzed against PBS (0.15M NaCl, 0.15M potassium phosphate, pH 7.2), overnight.

Dot blot assay

The virus preparation is spotted onto a strip of nitrocellulose (Schleicher and Schuell, BA 85) in 1 ul amounts and the paper allowed to dry. The blocking solution (BLOTTO, nonfat dry milk "Bovine Lacto Transfer Technique Optimizer 2.5%, (2.5% w/v nonfat dry milk, 0.01% antifoam A, Sigma Chemical Co., St. Louis, Mo.) is added for 30 minutes at 37° with agitation. The nitrocellulose strips are washed 3 times with Tris buffered saline (Tris, 10 mM, pH 8.0, Nacl 150 nM, Tween 20, 0.05% (TBST). The rabbit biotinylated antiviral IgG is then added (50 ug in 2 ml), incubated for 1 hr/37°, then washed with TBST, 3 times. Streptavidin-alkaline phosphatase (SAAP)(Jackson Immunoresearch Laboratories, Inc., West Grove, Pa.), 1 mg/ml, 1:7500, is added and the strips are incubated for 30 minutes at room temperature after washing with veronal acetate (0.15M, pH 9.6), 3 times. The coloring solution is added: 5-bromo-4 chloroindoxyl phosphate (BCIP), 5 mg/ml, 0.1 ml, nitroblue tetrazolium, 0.1%, 1 ml, $MgCl_2$, 2 M, 20 ul, and veronal acetate buffer, 9 ml. The nitrocellulose strips are agitated and the dots usually appear within 5 minutes. The nitrocellulose strips are washed once in $dH_2O$ and dried. The strips may be stored for use as reference standards, such as might be done with a kit for detection of avian influenza virus, or the strips ca be used for quantitation of virus.

Quantitation of virus

Quantitation of the amount of avian influenza virus in the sample may be done by densitometry following the procedure of Hazelgrove et al., Anal. Biochem 150:449–456, 1985). This procedure is based on a TV camera linked to a computer. The dots are displayed on a light box imaged by the TV camera, and digitized with a digitizing board (Techmar, Inc.). After digitizing, the computer will readout the position, width, height and relative area of each dot. Optical density (OD) measurements are plotted against absolute protein concentrations.

In FIG. 1, various dot blots derived from several different experiments are represented. FIG. 1*a* shows the relationship of color intensity and nanogram concentration of H5N2/Mal/NY/82 when probed with homologous biotinylated anti-H5N2 antibodies. Dots in FIG. 1 a (1) through (7) represent 10 ng, 5 ng, 2 ng, 1 ng, 0.5 ng, 0.25 and 0 ng virus protein, respectively. (In FIG. 1, the concentrations of virus are contained in 1 ul of blotted suspension). FIG. 1*b* shows the relationship of color intensity and nanogram concentration of H6N8/Ty/Mn/83 when probed with homologous biotinylated anti H6N8 antibodies. Dots in FIG. 1*b* (1) through (7) represent 20 ng, 10 ng, 5 ng, 2 ng, 1 ng, 0.5 ng and 0 ng virus protein, respectively. FIGS. 2*a* and 2*b* show the quantitative representation of viral protein after computer-analyzed digitation. As can be seen, 1–2 ng of H5N2 and 1–5 ng of H6N8 could be detected; the curves are linear.

In FIG. 1*c*, in order to test specificity of antibody, the purified H5N2 virus was initially dot blotted at 10 ng, 5 ng, 2 ng, and 1 ng concentrations, using the anti-H5N2 antibody FIG. 1*c* (1). In the adjacent panel in FIG. 1*c*(2), the biotinylated antibody was partially blocked with purified virus (8 ng virus absorbed to 450 ng antibody, and fully blocked with 16 ng virus in FIG. 1*c*(3).

In FIG. 1*d*, to test for antibody specificity, the purified H6N8 virus was dot blotted at concentrations ranging from 10 ng, 5 ng, 2 ng, and 1 ng/ul, using the homologous, biotinylated rabbit anti-H6N8 antibody preparation as shown in FIG. 1*d*(1). In the adjacent panel [FIG. 1*d*(2)], the biotinylated antibody was partially blocked with purified virus (8 ng virus absorbed to 450 ng/antibody), and fully blocked with 16 ng virus as shown in FIG. 1*d*(3).

Similarly, in FIG. 1*e*, using the H2N7 dot blot system (FIG. 1*e* (1), dots could be developed at I0 ng, 5 ng, and 1 ng/ul, and specific blocking of the biotinylated antibody with specific virus could be achieved panel, FIG. 1*e*(2)].

Fingerprinting Assay To Determine Viral Subtype Isoelectric Focusing and Transblotting Of Serum Proteins and Antibodies Polyclonal rabbit antisera are subjected to isoelectric focusing in flat beds of polyacrylamide of o.7 m thickness, pH range 5.5 to 8.0, 3 hours, 2° C., following the method of Wolf et al., "Clonal Diversity and Homology of Latent and Nominal Group a Immunoglobulin Allotypes in the Rabbit", Mol. Immunol. 21: 139-146, (1984). The focused proteins are transblotted to nitrocellulose paper (BA85, Schleicher and Schuell) overnight, by anodal or cathodal electrotransfer (50V, 2 mA), in 25 nM Tris, 192 mM glycine, pH 8.3 and 20% (v/v) methanol.

Probing the Transblotted Antibodies With Virus Followed By Biotinylated Anti-viral Antibodies (Sandwich Technique)

The nitrocellulose paper is removed from the transblotting cassette. Strips approximately 0.5 cm wide are cut along the migration path of the isoelectrofocused proteins. The strips are laid into troughs approximately 1.0 cm × 1.0 cm × 20 cm in a processing tray (Schleicher and Schuell). In succession the following steps are followed: blocking solution, 1% bovine serum albumin (BSA), 2 ml is added and the tray is rocked for 2 hours. The troughs are then drained thoroughly. At this point the strips may be used immediately to test for the presence of the virus or they may be dried and stored for future use, such as would be done with a kit for detection of avian influenza virus.

A 1:100 dilution of virus in PBS (for example H5N2, hemagglutinin titer 1:64) is added, and rocked for 1 hr/37° C. The wells are drained, biotinylated anti-H5N2 IgG is added (2 ml containing 20 ug), and incubated 1 hr/37° C. The wells are again drained and streptavidin-alkaline phosphatase is added (10 ug/ml), and incubated at room temperature, 30 minutes. The strips are washed with veronal buffer (3 times), the coloring solution, 5-bromo-4-chloroindoxyl phosphate (BCIP), 5 mg/ml, 0.1 ml, plus nitroblue tetrazolium (NBT), 0.1%, 1 ml, $MgCl_2$, 2M, 20 ul and veronal acetate buffer, 9 ml, is added, (as in the Dot Blot method), with the bands appearing in 5-10 minutes. The nitrocellulose strips are washed in distilled $H_2O$ and air dried. The bands may be quantitated using densitometry as described herein, following the procedure of Haselgrove supra.

In FIG. 3 (A) is seen a blot depicting the ability of hyperimmune sera from two different rabbits (R406 and 8401AJ) to react with H5N2/Mal/NY/82 virus. After transblotting at the cathode the virus was absorbed to the nitrocellulose strips and probed with biotinylated antibodies from the same two rabbits. Major bands developed, mainly between a pI range of 6.5 to 7.1, representing spectroptypes to virus epitopes. In lanes 4 and 5 the first eight bands, 1, 2a, 2b, 3 4, 5, 6 and 7, descending from the pI of 7.1 to 6.4 have been quantitatively computer-digitized and the line and bar graphs are represented in FIG. 4a and 4b (lane 4) and FIGS. 4c and 4d (lane 5).

Figure 3B:
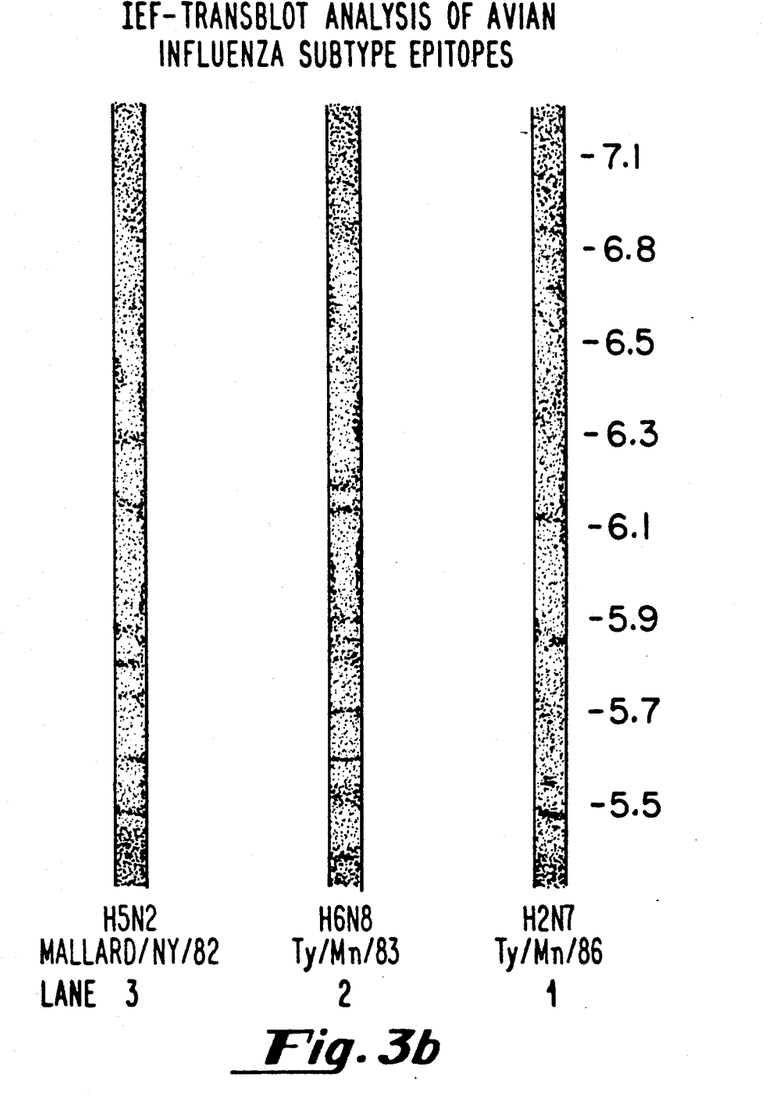

In FIG. 3(b), three blots of three different subtypes of avian influenza virus, are compared for epitope differences. The single antiserum to H5N2/Mal/Ny/82 was used to analyze each blot in FIG. 3. After isoelectric focusing and transblotting at the anode, the 3 different viruses were probed with the same biotinylated anti H5N2 antibodies.

Epitope differences in bands may be seen as well as identities throughout the blots. H6N8 shows band deficiencies (bands are not seen in comparison to H5N2) at pIs of 6.5, 6.3, 6.0 and 5.6. H2N7 shows band deficiencies at pIs of 6.5, 6.3, 6.0, 5.9, 5.7 and 5.6.

It is within the scope of the invention to test for virtually any antigen. Viral components such as hemagglutinins and neuraminidases show differences among subtypes and strains. Polyclonal antibodies to these viral components would be expected to show differences between subtypes and strains based on these differences. Polyclonal antibodies to appropriately chosen viral components would then yield a "fingerprint" of the viral component for each subtype or strain. These could then be used in the fingerprint assay as described herein, alone or in combination with antibodies specific for other viral components or whole virus.

Purification of hemagglutinin (HA)

After purification, the virus is dialyzed against 0.005M sodium phosphate buffer, pH 7.2, then extracted at 1 mg protein/ml in the same suffer containing Triton X-100 at 2%. The extract is separated from undissociated viral components at 100,000 xg/60 minutes. The extract is loaded to a DEAE-agarose column and eluted with a gradient from 0-0.2M NaCl, the protein being eluted mainly at 0.06M NaCl as monitored by SDS-PAGE, following the method of Wabuke-Bunoti et al, "Stimulation of Anti-Influenza Cytolitic T Lymphocytes by CNBr Cleavage Fragments of Viral Hemagglutinin", J. Immunol. 127: 1122-1125, (1981). Purity is confirmed by ELISA using antisera provided by D. Senne, USDA, Ames, Iowa; these antisera may also be employed for purposes of affinity purification of the HA, if contaminants are seen following biochemical purification.

Purification of neuraminidase

Purified viruses suspended in 2% $NH_4Cl$, 0.01M $(NH_4)_2HPO_4$ are disrupted with ammonium deoxycholate (final concentration, 0.2%), in the absence of $Na+$. The virus particles are allowed to stand for 5 hours/room temperature. Deoxycholate is dialyzed out. The proteins are pelleted at 200,000 xg at 6 hours. The pellet is resuspended in phosphate buffer with sonication. Nucleocapsids are separated on cellulose acetate strips and the neuraminidase is eluted from polyacrylamide gel after separation from the hemagglutinin. Purity of the neuraminidase is confirmed using antisera provided by D. Senne and anti-neuraminidase antisera may also be employed for purposes of affinity purification of the neuraminidase.

Quantitation of the methods of the invention would extend applications for the methods. For example, shared epitopes may be quantitated not only among viral subtypes, but also among strains within a viral subtype. Further the methods are highly sensitive. The level of sensitivity of the dot blot is at 1-5 ng antigen and in the "fingerprinting" assay, fewer than 10 ng of antigen protein may be detectable.

What is claimed is:

1. A method for detecting an antigen in a test sample suspected of containing said antigen and simultaneously determining a fingerprint of antibodies specific for said antigen, comprising the steps:
    (a) providing polyclonal antibodies specific for said antigen;

(b) separating said polyclonal antibodies specific for said antigen from each other according to the electrical charge of individual antibodies comprising said polyclonal antibodies;

(c) binding said antibodies thus separated to a solid support such that said antibodies separated in step (b) maintain the same relative position with respect to each other on said solid support to thereby form a fingerprint of antibodies specific for said antigen;

(d) contacting said antibodies bound in step (c) with a test sample suspected of containing said antigen under conditions selected to allow binding of said antigen to said antibodies bound in step (c);

(e) contacting antigen bound in step (d) with detectably labeled antibodies specific for said antigen, under conditions selected to allow binding of said detectably labeled antibodies to said antigen;

(f) detecting said detectably labeled antibody to thereby indicate the presence of said antigen in said test sample and reveal said fingerprint of antibodies specific for said antigen when said antigen is present in said test sample.

2. The method of claim 1 further comprising the step of quantitating the amount of said labeled antibody bound to said antigen and relating said amount to the amount of said antigen present in the test sample.

3. The method of claim 2 wherein the step of quantitating is be densitometric measurement.

4. The method of claim 1 further comprising the step of removing antibodies cross-reactive with antigens other than said antigen from said polyclonal antibodies before step (b).

5. The method of claim 1 wherein said detectably labeled antibody is labeled with biotin.

6. The method of claim 5 wherein said detectably labeled antibody is detected by
(a) contacting said biotin with streptavidin-alkaline phosphate under conditions selected to allow the streptavidin-alkaline phosphatase to bind to said biotin;
(b) contacting said streptavidin-alkaline phosphatase with a chromogenic substrate suitable for alkaline phosphatase; and
(c) detecting a reaction product of said chromogenic substrate.

7. The method of claim 1 wherein said antigen is a viral protein.

8. The method of claim 7 wherein said viral protein is an avian influenza viral protein.

9. The method of claim 1 wherein said solid support is nitrocellulose.

10. The method of claim 1 wherein the step of separating said polyclonal antibodies is performed by isoelectric focusing.

11. A kit for identification of an antigen in a test sample suspected of containing said antigen, comprising:
(a) a solid support having bound thereon polyclonal antibodies specific for said antigen, said antibodies having been separated from each other according to the electrical charge of the individual antibodies comprising the polyclonal antibodies and bound to said solid support such that the separated antibodies maintain the same relative position with respect to the each other on said solid support;
(b) a reagent comprising antibodies specific for said antigen labeled with a detectable label;
(c) at least one reagent comprising means for detecting said detectable label in (b); and
(d) reference standard of said antigen.

12. The kit of claim 11 wherein said solid support is nitrocellulose.

13. The kit of claim 11 wherein the separation of said polyclonal antibodies is achieved by isoelectric focusing.

14. The kit of claim 11 wherein said antigen is a viral protein.

15. The kit of claim 23 wherein said viral protein is an avian influenza viral protein.

16. A method for detecting an antigen in a test sample suspected of containing said antigen and simultaneously determining a fingerprint of antibodies specific for said antigen, comprising the steps:
(a) providing a solid support having bound thereon polyclonal antibodies specific for said antigen, said antibodies having been separated from each other according to the electrical charge of the individual antibodies making up the polyclonal antibodies and bound to said solid support such that the said antibodies thus separated maintain the same relative position with respect to each other on said solid support to thereby form a fingerprint of antibodies specific for said antigen;
(b) contacting said solid support with a test sample suspected of containing said antigen under conditions selected to allow binding of said antigen to said antibodies bound on said solid support;
(c) contacting said antigen thus bound on said solid support in step (b) with detectably labeled antibody specific for said antigen under conditions selected to allow binding of said antibody to said antigen;
(d) detecting said detectably labeled antibody thus bound in step (c) to thereby indicate the presence of said antigen in said test sample and reveal said fingerprint of antibodies specific for said antigen when said antigen is present in said test sample.

17. The method of claim 16 further comprising the step of quantitating the amount of said detectably labeled antibody bound to said antigen and relating said amount to the amount of said antigen present in the test sample.

18. The method of claim 17 wherein the step of quantitating is by densitometric measurement.

19. The method of claim 29 wherein said detectably labeled antibody is labeled with biotin.

20. The method of claim 32 wherein said detectably labeled antibody is detected by
(a) contacting said biotin with streptavidin-alkaline phosphatase under condition selected to allow the streptavidin-alkaline phosphatase to bind to said biotin;
(b) contacting said streptavidin-alkaline phosphatase with a chromogenic substrate suitable for alkaline phosphatase; and
(c) detecting a reaction product of said chromogenic substrate.

21. The method of claim 16 wherein said antigen is a viral protein.

22. The method of claim 21 wherein said viral protein is an avian influenza viral protein.

23. The method of claim 16 wherein said solid support is nitrocellulose.

24. The method of claim 1 further comprising the step of
comparing said fingerprint of antibodies of step (f) with a fingerprint of antibodies specific for a reference standard of said antigen.

25. The method of claim 16 further comprising the step of
comparing said fingerprint of antibodies of step (d) with a fingerprint of antibodies specific for a reference standard of said antigen.

* * * * *

UNITED STATES PATENT AND TRADEMARK OFFICE
CERTIFICATE OF CORRECTION

PATENT NO. : 5,225,322

DATED : July 6, 1993

INVENTOR(S) : Benjamin Wolf

It is certified that error appears in the above-identified patent and that said Letters Patent is hereby corrected as shown below:

Column 3, line 12, after isotype insert "."

Column 5, line 58, after 3A, delete "show" and insert therefor "shows"

Column 5, line 62, after shows, insert "a"

Column 6, line 33, after separates, delete "antibodies" and insert therefor "antibody"

Column 11, line 42, after "100,000", delete "Xg" and insert therefor "xg"

Column 12, line 15, delete "ca" and insert therefor "can"

Column 12, line 65, after at, delete "I0" and insert therefor "10"

Column 12, line 67, after achieved, delete "panel," and insert therefor "as shown in"

Column 12, line 68, before ".", delete "]"

Column 13, line 6, before m, delete "o.7" and insert therefor "0.7"

UNITED STATES PATENT AND TRADEMARK OFFICE
CERTIFICATE OF CORRECTION

PATENT NO. : 5,225,322
DATED : July 6, 1993
INVENTOR(S) : Benjamin Wolf

It is certified that error appears in the above-indentified patent and that said Letters Patent is hereby corrected as shown below:

Column 16, line 46, after under, delete "condition" and insert therefor --conditions--.

Signed and Sealed this

Eighth Day of November, 1994

Attest:

BRUCE LEHMAN

Attesting Officer  Commissioner of Patents and Trademarks